US012616393B2

(12) United States Patent
Johnson et al.

(10) Patent No.: US 12,616,393 B2
(45) Date of Patent: May 5, 2026

(54) WEARABLE DEVICE WITH STATUS DISPLAY

(71) Applicant: Toshiba Global Commerce Solutions, Inc., Durham, NC (US)

(72) Inventors: Brad M. Johnson, Raleigh, NC (US); John Pistone, Durham, NC (US); Frank James, Durham, NC (US)

(73) Assignee: Toshiba Global Commerce Solutions, Inc., Durham, NC (US)

( * ) Notice: Subject to any disclaimer, the term of this patent is extended or adjusted under 35 U.S.C. 154(b) by 1019 days.

(21) Appl. No.: 17/710,558

(22) Filed: Mar. 31, 2022

(65) Prior Publication Data

US 2023/0309862 A1    Oct. 5, 2023

(51) Int. Cl.
*A61B 5/11* (2006.01)
*A61B 5/00* (2006.01)
(Continued)

(52) U.S. Cl.
CPC .......... *A61B 5/1118* (2013.01); *A61B 5/0017* (2013.01); *A61B 5/6815* (2013.01); *H04W 4/38* (2018.02); *H04W 4/80* (2018.02)

(58) Field of Classification Search
CPC ... A61B 5/1118; A61B 5/0017; A61B 5/6815; A61B 5/0022; A61B 5/163; A61B 5/6898; A61B 5/0205; A61B 5/05; A61B 5/024; H04W 4/38; H04W 76/14; H04W 76/27; G06F 3/017; G06F 3/00; G06F 3/01; G06F 3/011; G06F 3/012; G06F 3/013; G06F 3/002; G06F 3/007; G06F 3/05; G06F 3/06; G06F 3/09; G06F 3/12; G06F 3/13; G06F 3/14; G06F 3/16; G06F 3/04842; G06F 3/015; H04R 1/1016; H04R 25/55; H04R 5/033; H04R 2420/07; H04R 2460/07; H04M 1/05; H04M 1/6066;
(Continued)

(56) References Cited

U.S. PATENT DOCUMENTS

2012/0296191 A1   11/2012   McGrath et al.
2018/0048750 A1    2/2018   Hardi
2021/0105353 A1*   4/2021   Llewelyn .............. G06F 1/1684

FOREIGN PATENT DOCUMENTS

CA      3059789 A1 *  11/2018   ........... G02B 27/017
CN     208384242 U  *   1/2019
KR   20170019816 A  *   2/2017   ............. H04N 23/62

* cited by examiner

*Primary Examiner* — Brian A Zimmerman
*Assistant Examiner* — Anthony D Afrifa-Kyei
(74) *Attorney, Agent, or Firm* — Kaufman & Canoles P.C.

(57) ABSTRACT

Systems and methods of visually indicating a current user activity or status on a display of an ear wearable device are provided. In one exemplary embodiment, a method comprises, by an ear wearable device that includes a display that is configured to be viewable while the ear wearable device is worn, receiving, from a first network node over a wireless communication channel, a first display object of a set of display objects that represents user activity or status associated with the ear wearable device or an indication associated with the first display object, with each display object being configured for display on the display of the ear wearable device so as to visually indicate the current user activity or status, the first network node being enabled to determine the current user activity or status and obtain the first display object based on the current user activity or status.

20 Claims, 9 Drawing Sheets

(51) Int. Cl.
*H04W 4/38*          (2018.01)
*H04W 4/80*          (2018.01)
(58) Field of Classification Search
CPC ... H04M 2250/10; G16H 20/30; G16H 20/00;
G16H 40/63; A63B 24/0062; A63B
71/06; A63B 71/0622; A63B 2071/065;
A63B 2071/0675; A63B 2071/0694;
G08B 21/18
See application file for complete search history.

200a

200b

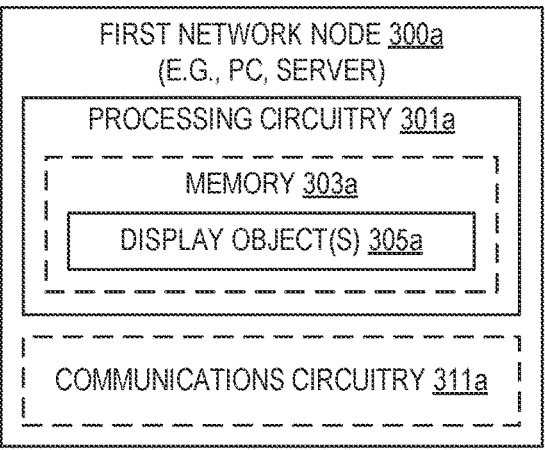

FIRST NETWORK NODE 300a
(E.G., PC, SERVER)

PROCESSING CIRCUITRY 301a

MEMORY 303a

DISPLAY OBJECT(S) 305a

COMMUNICATIONS CIRCUITRY 311a

FIG. 3A

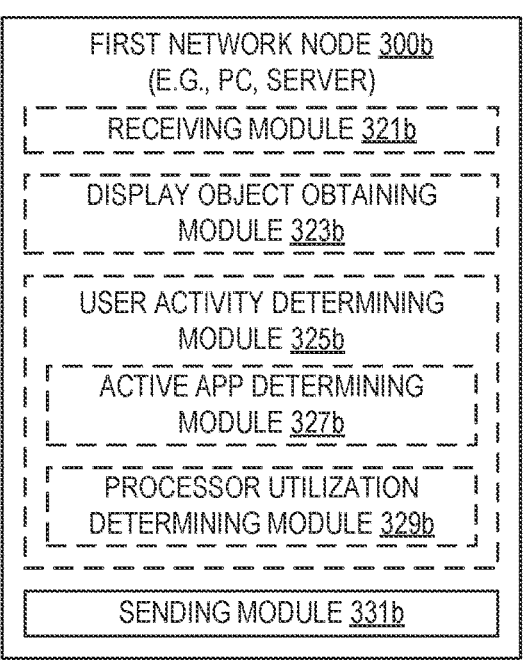

FIRST NETWORK NODE 300b
(E.G., PC, SERVER)

RECEIVING MODULE 321b

DISPLAY OBJECT OBTAINING
MODULE 323b

USER ACTIVITY DETERMINING
MODULE 325b

ACTIVE APP DETERMINING
MODULE 327b

PROCESSOR UTILIZATION
DETERMINING MODULE 329b

SENDING MODULE 331b

FIG. 3B

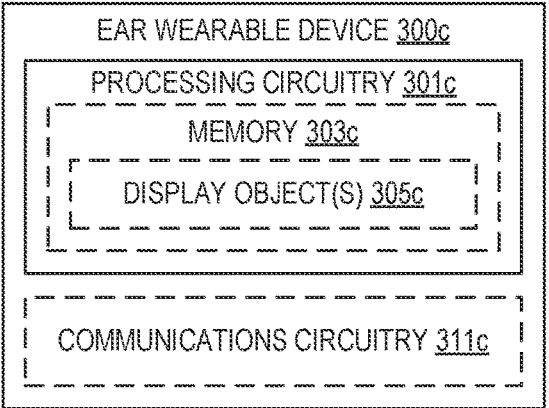

EAR WEARABLE DEVICE 300c

PROCESSING CIRCUITRY 301c

MEMORY 303c

DISPLAY OBJECT(S) 305c

COMMUNICATIONS CIRCUITRY 311c

FIG. 3C

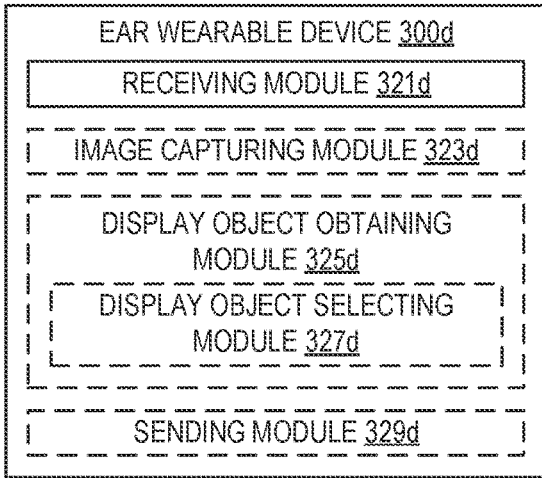

EAR WEARABLE DEVICE 300d

RECEIVING MODULE 321d

IMAGE CAPTURING MODULE 323d

DISPLAY OBJECT OBTAINING
MODULE 325d

DISPLAY OBJECT SELECTING
MODULE 327d

SENDING MODULE 329d

FIG. 3D

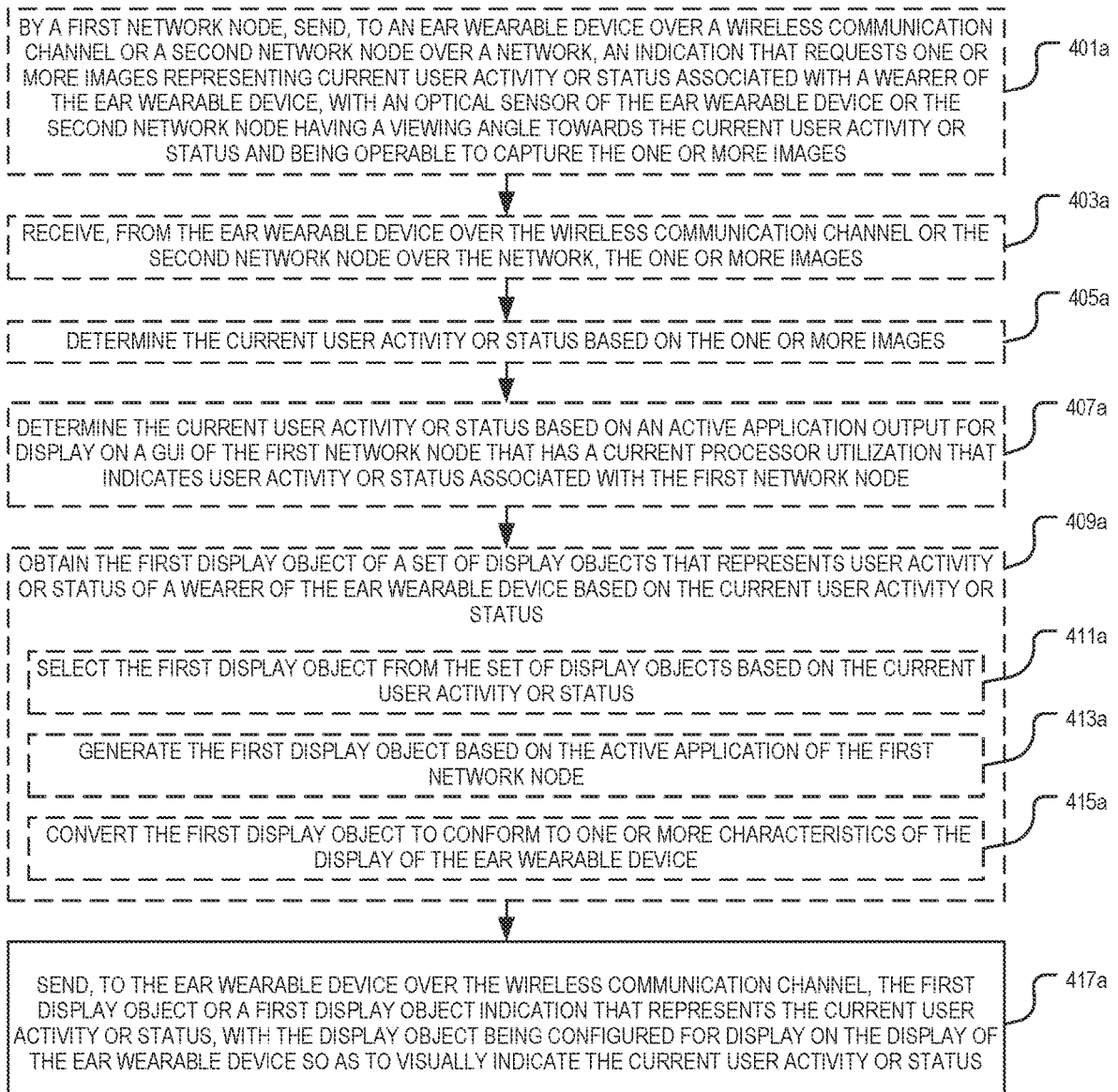

400a

BY A FIRST NETWORK NODE, SEND, TO AN EAR WEARABLE DEVICE OVER A WIRELESS COMMUNICATION CHANNEL OR A SECOND NETWORK NODE OVER A NETWORK, AN INDICATION THAT REQUESTS ONE OR MORE IMAGES REPRESENTING CURRENT USER ACTIVITY OR STATUS ASSOCIATED WITH A WEARER OF THE EAR WEARABLE DEVICE, WITH AN OPTICAL SENSOR OF THE EAR WEARABLE DEVICE OR THE SECOND NETWORK NODE HAVING A VIEWING ANGLE TOWARDS THE CURRENT USER ACTIVITY OR STATUS AND BEING OPERABLE TO CAPTURE THE ONE OR MORE IMAGES — 401a

RECEIVE, FROM THE EAR WEARABLE DEVICE OVER THE WIRELESS COMMUNICATION CHANNEL OR THE SECOND NETWORK NODE OVER THE NETWORK, THE ONE OR MORE IMAGES — 403a

DETERMINE THE CURRENT USER ACTIVITY OR STATUS BASED ON THE ONE OR MORE IMAGES — 405a

DETERMINE THE CURRENT USER ACTIVITY OR STATUS BASED ON AN ACTIVE APPLICATION OUTPUT FOR DISPLAY ON A GUI OF THE FIRST NETWORK NODE THAT HAS A CURRENT PROCESSOR UTILIZATION THAT INDICATES USER ACTIVITY OR STATUS ASSOCIATED WITH THE FIRST NETWORK NODE — 407a

OBTAIN THE FIRST DISPLAY OBJECT OF A SET OF DISPLAY OBJECTS THAT REPRESENTS USER ACTIVITY OR STATUS OF A WEARER OF THE EAR WEARABLE DEVICE BASED ON THE CURRENT USER ACTIVITY OR STATUS — 409a

SELECT THE FIRST DISPLAY OBJECT FROM THE SET OF DISPLAY OBJECTS BASED ON THE CURRENT USER ACTIVITY OR STATUS — 411a

GENERATE THE FIRST DISPLAY OBJECT BASED ON THE ACTIVE APPLICATION OF THE FIRST NETWORK NODE — 413a

CONVERT THE FIRST DISPLAY OBJECT TO CONFORM TO ONE OR MORE CHARACTERISTICS OF THE DISPLAY OF THE EAR WEARABLE DEVICE — 415a

SEND, TO THE EAR WEARABLE DEVICE OVER THE WIRELESS COMMUNICATION CHANNEL, THE FIRST DISPLAY OBJECT OR A FIRST DISPLAY OBJECT INDICATION THAT REPRESENTS THE CURRENT USER ACTIVITY OR STATUS, WITH THE DISPLAY OBJECT BEING CONFIGURED FOR DISPLAY ON THE DISPLAY OF THE EAR WEARABLE DEVICE SO AS TO VISUALLY INDICATE THE CURRENT USER ACTIVITY OR STATUS — 417a

FIG. 4A

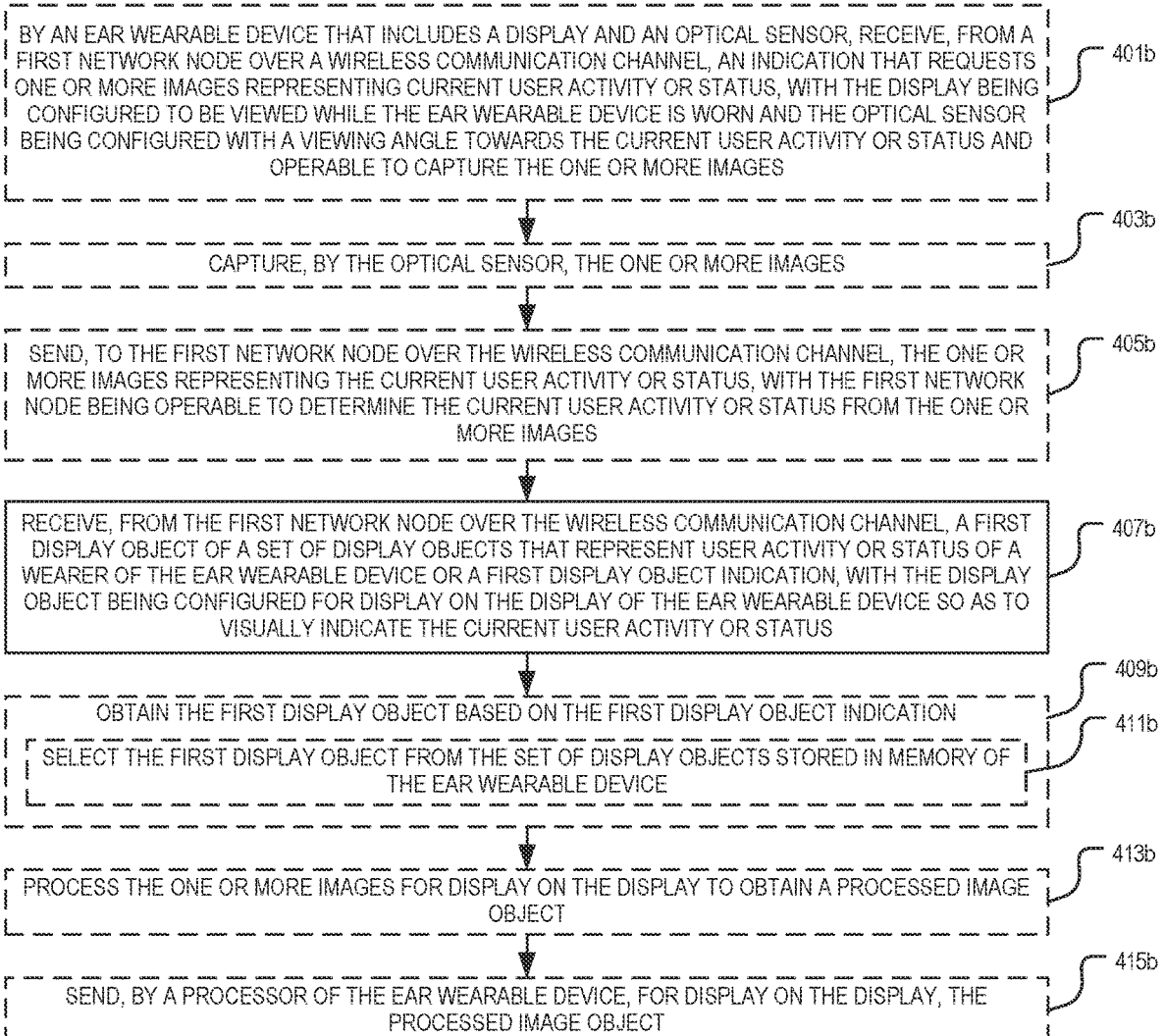

400b

BY AN EAR WEARABLE DEVICE THAT INCLUDES A DISPLAY AND AN OPTICAL SENSOR, RECEIVE, FROM A FIRST NETWORK NODE OVER A WIRELESS COMMUNICATION CHANNEL, AN INDICATION THAT REQUESTS ONE OR MORE IMAGES REPRESENTING CURRENT USER ACTIVITY OR STATUS, WITH THE DISPLAY BEING CONFIGURED TO BE VIEWED WHILE THE EAR WEARABLE DEVICE IS WORN AND THE OPTICAL SENSOR BEING CONFIGURED WITH A VIEWING ANGLE TOWARDS THE CURRENT USER ACTIVITY OR STATUS AND OPERABLE TO CAPTURE THE ONE OR MORE IMAGES                                                   401b

CAPTURE, BY THE OPTICAL SENSOR, THE ONE OR MORE IMAGES                                         403b

SEND, TO THE FIRST NETWORK NODE OVER THE WIRELESS COMMUNICATION CHANNEL, THE ONE OR MORE IMAGES REPRESENTING THE CURRENT USER ACTIVITY OR STATUS, WITH THE FIRST NETWORK NODE BEING OPERABLE TO DETERMINE THE CURRENT USER ACTIVITY OR STATUS FROM THE ONE OR MORE IMAGES                                                                            405b

RECEIVE, FROM THE FIRST NETWORK NODE OVER THE WIRELESS COMMUNICATION CHANNEL, A FIRST DISPLAY OBJECT OF A SET OF DISPLAY OBJECTS THAT REPRESENT USER ACTIVITY OR STATUS OF A WEARER OF THE EAR WEARABLE DEVICE OR A FIRST DISPLAY OBJECT INDICATION, WITH THE DISPLAY OBJECT BEING CONFIGURED FOR DISPLAY ON THE DISPLAY OF THE EAR WEARABLE DEVICE SO AS TO VISUALLY INDICATE THE CURRENT USER ACTIVITY OR STATUS                                          407b

OBTAIN THE FIRST DISPLAY OBJECT BASED ON THE FIRST DISPLAY OBJECT INDICATION                    409b

SELECT THE FIRST DISPLAY OBJECT FROM THE SET OF DISPLAY OBJECTS STORED IN MEMORY OF THE EAR WEARABLE DEVICE                                                                               411b

PROCESS THE ONE OR MORE IMAGES FOR DISPLAY ON THE DISPLAY TO OBTAIN A PROCESSED IMAGE OBJECT                                                                                          413b

SEND, BY A PROCESSOR OF THE EAR WEARABLE DEVICE, FOR DISPLAY ON THE DISPLAY, THE PROCESSED IMAGE OBJECT                                                                            415b

FIG. 4B

WEARABLE DEVICE WITH STATUS DISPLAY

BACKGROUND

Wearable technology is a category of electronic devices that can be worn as accessories, embedded in clothing, or implanted in the user's body. The devices are hands-free gadgets with practical uses, powered by microprocessors and enhanced with the ability to send and receive data via the Internet. Further, wearable technology (e.g., headsets) has been integrated into communication systems in the retail environment and is becoming a necessary part of retail operational efficiency.

BRIEF DESCRIPTION OF THE DRAWINGS

The present disclosure will now be described more fully hereinafter with reference to the accompanying drawings, in which embodiments of the disclosure are shown. However, this disclosure should not be construed as limited to the embodiments set forth herein. Rather, these embodiments are provided so that this disclosure will be thorough and complete, and will fully convey the scope of the disclosure to those skilled in the art. Like numbers refer to like elements throughout.

FIGS. 3A-B illustrate other embodiments of a first network node in accordance with various aspects as described herein.

FIGS. 3C-D illustrate other embodiments of an ear wearable device in accordance with various aspects as described herein.

FIG. 4A illustrates one embodiment of a method performed by a first network node of visually indicating a current user activity or status on a display of an ear wearable device in accordance with various aspects as described herein.

FIG. 4B illustrates another embodiment of a method performed by an ear wearable device of visually indicating a current user activity or status on a display of the ear wearable device in accordance with various aspects as described herein.

DETAILED DESCRIPTION

For simplicity and illustrative purposes, the present disclosure is described by referring mainly to an exemplary embodiment thereof. In the following description, numerous specific details are set forth in order to provide a thorough understanding of the present disclosure. However, it will be readily apparent to one of ordinary skill in the art that the present disclosure may be practiced without limitation to these specific details.

Wearable technology continues to be a beneficial means for communications between retail store personnel in a retail environment. However, such wearable technology has been limited to voice communications with only retail store personnel being authorized to access voice communications enabled by the wearable technology. As such, only the store personnel receiving the voice communications from the wearer of the wearable technology can recognize the current activity or status of the wearer. Embodiments of the present disclosure recognize a lack of solutions for visually communicating with customers in the retail environment using wearable technology, such as, for example, headsets. Accordingly, there is a need for improved techniques for utilizing wearable technology to provide some level of communication to certain subjects within the retail environment that do have access to the communication systems of the retail environment.

In this disclosure, systems and methods of visually indicating a current user activity or status on a display of an ear wearable device are provided. In addition to providing voice communication, the ear wearable device includes a display configured to display the current activity or status of the wearer so that others can readily recognize such activity or status of the wearer. In a retail environment, store personnel and customers will recognize the current activity or status of the wearer by merely viewing the display of the wearable device. In one example, the display of the wearable device can indicate that the wearer is available (e.g., green display), soon to be available (e.g., yellow display), or not available (e.g., red display) to provide service to a customer. In another example, the display of the wearable device can indicate a certain emoji that represents the current activity or status of the wearer. Each emoji can represent a different activity or status of the wearer such as which stage of a sales process the wearer is conducting with a customer or the type of activity that the wearer is conducting. In yet another example, the display of the wearable device can indicate a quick response (QR) code that links to a website that provides the current activity or status of the wearer.

Figure 1A:
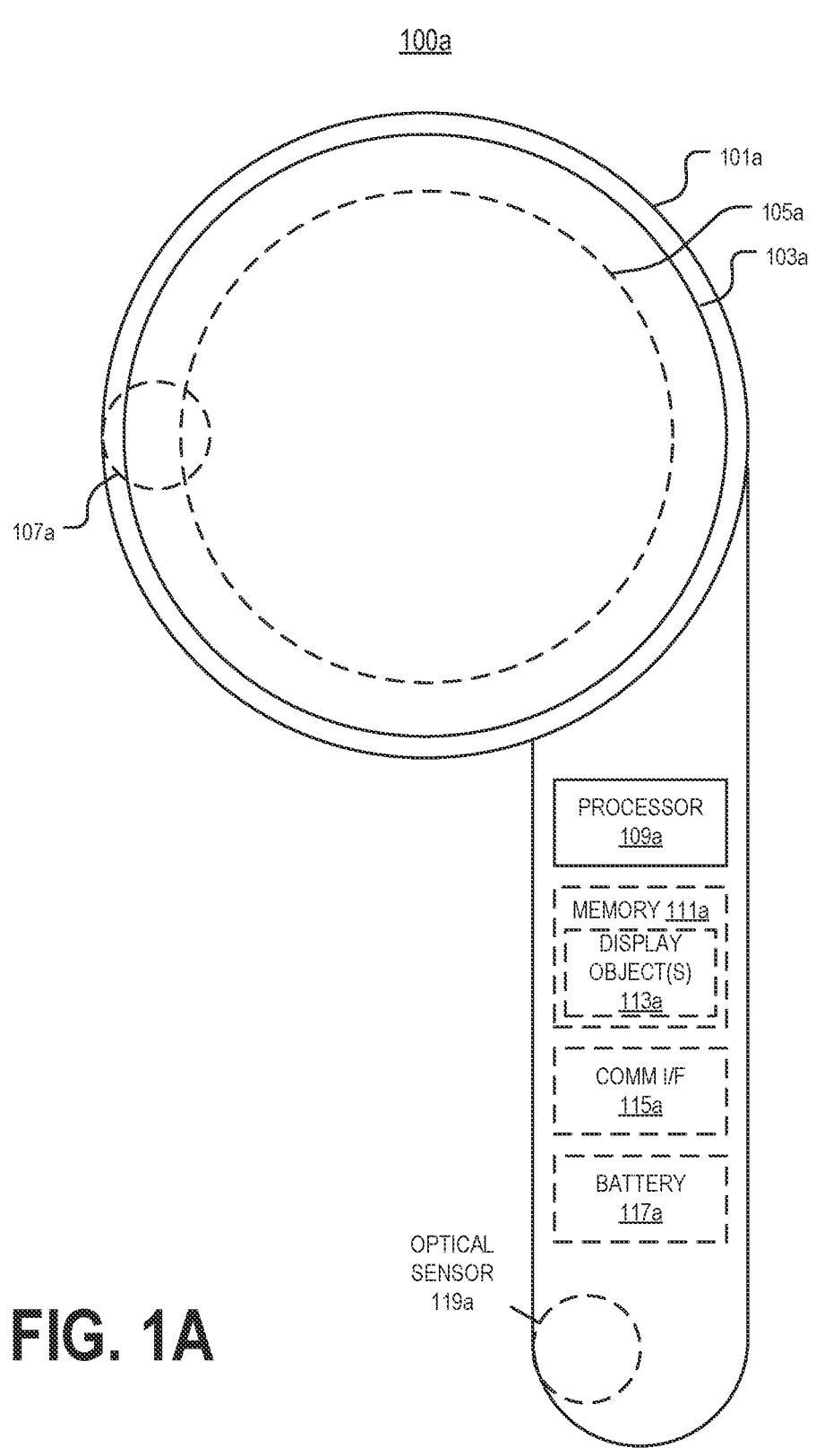
FIG. 1A illustrates one embodiment of an ear wearable device that visually indicates a current user activity or status on a display of the ear wearable device while being worn by a user in accordance with various aspects as described herein.

FIG. 1A illustrates one embodiment of an ear wearable device 100a that visually indicates a current user activity or status on a display 103a of that device 100a while being worn by a user in accordance with various aspects as described herein. In FIG. 1A, the ear wearable device 100a includes a housing 101a and a processor 109a operationally coupled to a display 103a, an audio output device 105a (e.g., speaker), an audio input device 107a (e.g., microphone), a memory 111a, a communication interface 115a, a battery 117a, an optical sensor 119a (e.g., camera), the like, or any combination thereof. The display 103a is configured to be viewable while the device 100a is worn. The memory 111a includes volatile or non-volatile memory. In some implementations, the memory 111a includes all or a portion of a set of display objects 113a stored in the memory 111a, with each display object 113a being configured for display on the display 103a. By having the display objects 113a stored in memory 111a, the device 100a can receive from a network node (e.g., PC, server) an indication of which display object to display on the display 103a of the device 100a instead of receiving the display object itself from the network node. Each display object 113a may include an image or sequence of images, textual data, an emoji, a QR code or any other object that may be displayed on the display 103a that visually indicates a current user activity or status of a wearer of the device 100*a*. The communication interface 115*a* is operable to send or receive information using any wired or wireless communication technology. In one example, the device 100*a* can receive one of a set of display objects and then store that display object in memory 111*a* such as for later selection by the network node by sending an indication to display that display object on the display 103*a*. In another example, the device 100*a* can receive one of the set of display objects and then send that display object for display on the display 103*a*. In yet another example, device 100*a* can receive an indication associated with one of the set of display objects and in response, send that display object for display on the display 103*a*.

Figure 1B:
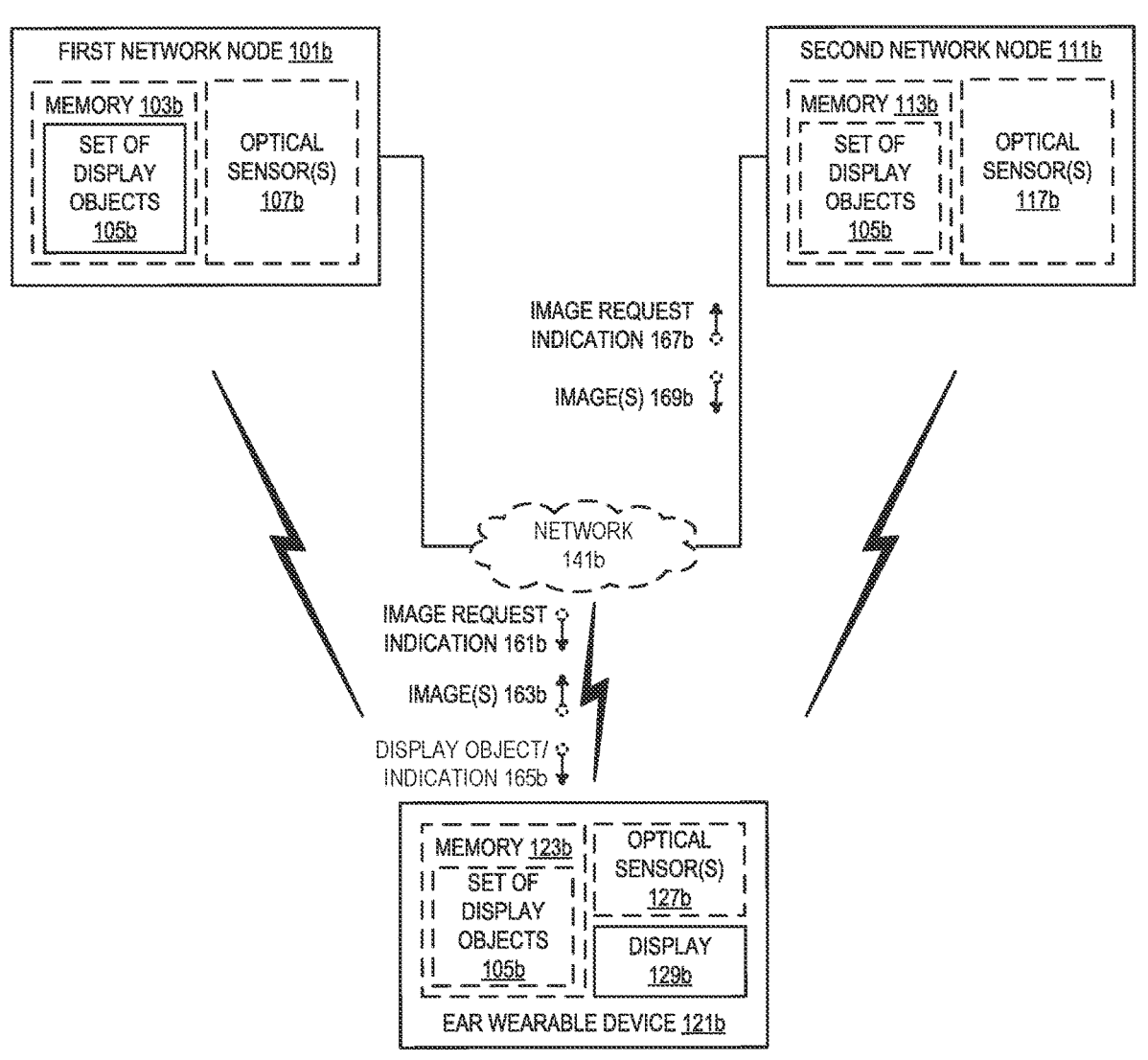
FIG. 1B illustrates one embodiment of a system that visually indicates a current user activity or status of a user on a display of the ear wearable device of FIG. 1A in accordance with various aspects as described herein.

FIG. 1B illustrates one embodiment of a system 100*b* that visually indicates a current user activity or status on a display 129*b* of an ear wearable device 121*b* in accordance with various aspects as described herein. In FIG. 1B, the system 100*b* includes first and second network nodes 101*b*, 111*b* and the ear wearable device 121*b*. The first network node 101*b* may include a memory 103*b* and an optical sensor 107*b* (e.g., camera). The second network node 111*b* may also include a memory 113*b* and an optical sensor 115*b* (e.g., camera). The ear wearable device 121*b* may include a memory 123*b*, an optical sensor 127*b* (e.g., camera), and the display 129*b*. Each memory 103*b*, 113*b*, 123*b* may include all or a portion of a set of display objects 105*b*, 115*b*, 125*b* that represents user activity or status of a wearer of the ear wearable device 121*b*. The first network node 101*b* and the second network node 111*b* can communicate over a wired or wireless communication channel of network 141*b* (e.g., WiFi, Ethernet, Internet). Further, the ear wearable device 121*b* can communicate with the first and second network nodes 101*b*, 111*b* over a wireless communications channel of the network 141*b* (e.g., WiFi, cellular) or a peer-to-peer wireless communications technology (e.g., Bluetooth, WiFi Direct). All or a portion of the network 141*b* may be implemented using a wired or wireless wide area network (WAN) (e.g., Internet, cellular), a wired or wireless local area network (LAN) (e.g., Bluetooth, Wi-Fi), or any combination or derivatives thereof. In one example, the first and second network nodes 101*b*, 111*b* and the ear wearable device 121*b* can communicate over the network 141*b*. In another example, the ear wearable device 121*b* can communicate with the first or second network nodes 101*b*, 111*b* over a peer-to-peer wireless communications channel.

In one embodiment, the first network node 101*b* sends, to the ear wearable device 121*b* over a wireless communication channel, an indication 161*b* that requests the ear wearable device 121*b* to send one or more images captured by the optical sensor(s) 127*b* having a viewing angle towards the current user activity or status such as consistent with a viewing angle of a wearer of the ear wearable device 121*b*. In one example, the viewing angle of the optical sensor(s) 127*b* can be towards a display of a wireless device (e.g., smartphone) operated by the wearer of the ear wearable device 121*b*. As such, the corresponding captured image(s) includes the subject matter of the display of the wireless device, which can be used by the first network node 101*b* to determine the current user activity or status of the wearer of the ear wearable device 121*b*. The ear wearable device 121*b* receives the image request indication 161*b* and in response, captures the one or more images from the optical sensor(s) 127*b*. The ear wearable device 121*b* then sends, to the first network node 101*b* over the wireless communication channel, the one or more images 163*b*.

Furthermore, the first network node 101*b* receives the one or more images 163*b* and in response, determines the current user activity or status associated with the wearer of the ear wearable device 121*b*. The first network node 101*b* may utilize a machine learning model that is trained with predetermined images of user activities or status of a wearer of the ear wearable device 121*b*. Further, the first network node 101*b* obtains the display object 105*b* from the set of display objects 105*b* based on the current user activity or status. In one example, the first network node 101*b* can generate the display object to form or add to the set of display objects 105*b* based on the current user activity or status. The first network node 101*b* may also convert the display object to conform to one or more characteristics (e.g., shape, size, pixels) of the display 129*b* of the ear wearable device 121*b*.

In the current embodiment, the first network node 101*b* sends, to the ear wearable device 121*b* over the wireless communication channel, the display object or an indication associated with the display object, as shown by reference 165*b*. For the first network node 101*b* sending a display object, the ear wearable device 121*b* receives the display object and in response, sends the display object for display on the display 127*b*. Alternatively or additionally, the ear wearable device 121*b* stores the display object in memory 123*b* for selection by the first network node 101*b*. For the first network node 101*b* sending a display object indication, the ear wearable device 121*b* receives the indication and in response, obtains from memory 123*b* the display object that corresponds to that indication. The ear wearable device 121*b* then sends the display object for display on the display 129*b*.

In another embodiment, the first network node 101*b* sends, to the second network node 111*b* over the network 141*b*, an indication 167*b* that requests the second network node 111*b* to send one or more images captured by the optical sensor(s) 117*b* having a viewing angle towards the current user activity or status of the wearer of the ear wearable device 121*b*. In one example, the viewing angle of the optical sensor(s) 117*b* can be towards a display of a wireless device (e.g., smartphone) operated by the wearer of the ear wearable device 121*b*. As such, the corresponding captured image(s) includes the subject matter of the display of the wireless device, which can be used by the first network node 101*b* to determine the current user activity or status of the wearer of the ear wearable device 121*b*. The second network node 111*b* receives the image request indication 167*b* and in response, captures the one or more images from the optical sensor(s) 117*b*. The second network node 111*b* then sends, to the first network node 101*b* over the network 141*b*, the one or more images 169*b*. The first network node 101*b* receives the one or more images 169*b* and in response, determines a current user activity or status associated with the wearer of the ear wearable device 121. Further, the first network node 101*b* obtains the display object from the set of display objects 105*b* based on the current user activity or status. The first network node 101*b* then sends, to the ear wearable device 121*b* over the wireless communication channel, the display object or the display object indication, as shown by reference 165*b*.

In another embodiment, the first network node 101*b* captures one or more images from the optical sensor(s) 107*b* having a viewing angle towards the current user activity or status of the wearer of the ear wearable device 121*b*. The first network node 101*b* then determines a current user activity or status associated with the wearer of the ear wearable device 121. Further, the first network node 101*b* obtains the display object from the set of display objects 105*b* based on the current user activity or status. The first network node 101*b* then sends, to the ear wearable device 121b over the wireless communication channel, the display object or the display object indication, as shown by reference 165b.

In another embodiment, the second network node 111b or the ear wearable device 121b can be configured to capture and send the one or more images at a certain time interval so that the current user activity or status can be updated on the display 129b of the ear wearing device 121b at the certain time interval. In one example, the certain time interval represents an amount of time to reasonably indicate a change in the current user activity or status of a wearer of the ear wearable device 121b. In another example, the certain time interval is in the range of one second to one hour, depending on the activity or status of the wearer.

In another embodiment, the first network node 101b can determine that a current processor utilization associated with a certain application executed by the first network node 101b and associated with the wearer of the ear wearable device 121b indicates user activity or status (e.g., editing a sales agreement, listening to music, drafting a text message, etc.). The first network node 101b can also receive one or more images from the optical sensor(s) 107b to determine that the wearer of the ear wearable device is operating the first network node 101b.

In another embodiment, the first network node 101b generates a display object/indication 165b associated with the current user activity or status. For example, the first network node 101b may retrieve a display object from the set of display objects 105b in the memory 103b based on the current user activity or status. In this example, the network node 101 may associate the display object and the current user activity or status using respective classifications. In another example, the first network node 101b may render a display object based on image data (e.g., icons, logos, etc.) associated with an active application. In yet another example, the first network node 101b may utilize textual or image data associated with an active application to generate a display object, such as, for example, text, emoticons, quick response (QR) codes, etc. In some implementations, the first network node 101b may utilizes data (e.g., resolution, aspect ratio, etc.) of the display 129b to configure a display object for display on the ear wearable device 121b.

Figure 2A:
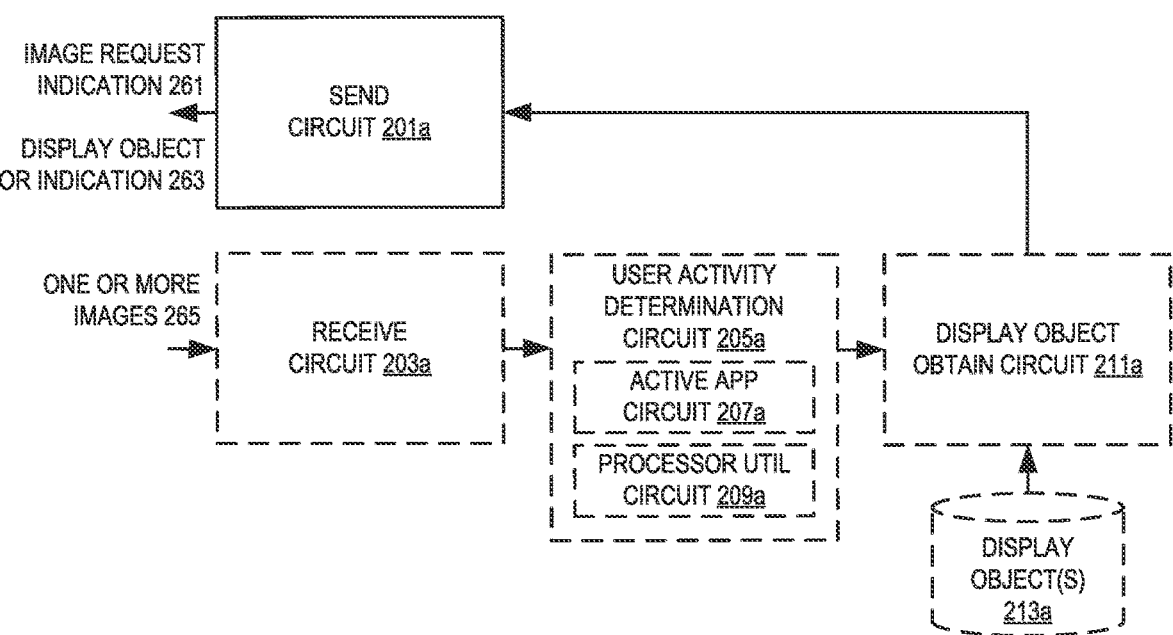
FIG. 2A illustrates one embodiment of a first network node in accordance with various aspects as described herein.
Figure 2B:
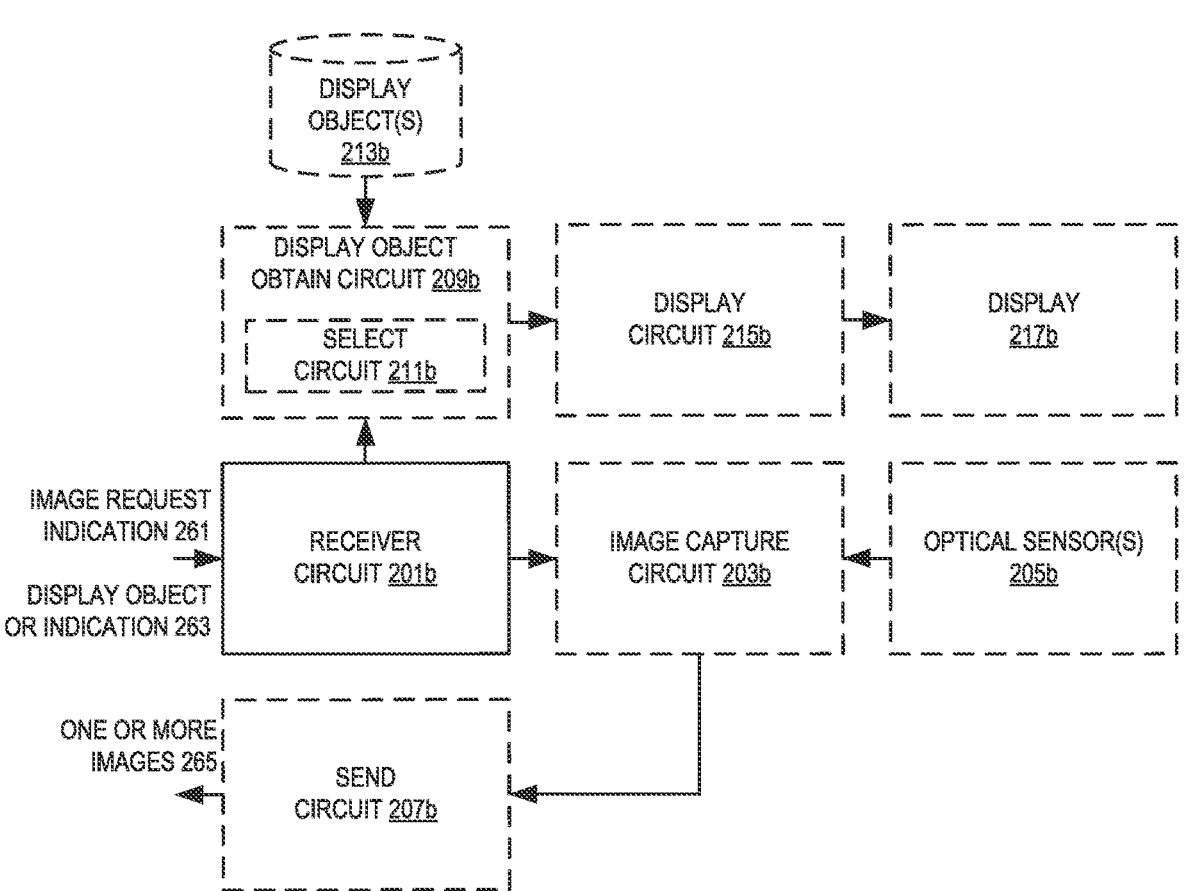
FIG. 2B illustrates one embodiment of an ear wearable device in accordance with various aspects as described herein.

FIGS. 2A-B illustrate embodiments of a first network node 200a and an ear wearable device 200b, respectively, in accordance with various aspects as described herein. In FIG. 2A, the device 200a implements various functional means, units, or modules (e.g., via the processing circuitry 301a in FIG. 3A, via the processing circuitry 501 in FIG. 5A, via software code, or the like), or circuits. In one embodiment, these functional means, units, modules, or circuits (e.g., for implementing the method(s) herein) may include for instance: a send circuit 201a operable to send an indication that requests one or more images representing a current user activity or status of a wearer of the ear wearable device 200b or to send a display object or an indication associated with the display object that represents the current user activity or status; a receive circuit 203a operable to receive one or more images representing the current user activity or status; a user activity determination circuit 205a operable to determine the current user activity or status based on the one or more images; an active application determination circuit 207a operable to determine an application output for display on a graphical user interface (GUI) of the device 200a that would indicate the certain user activity or status; a processor utilization circuit 209a operable to determine that the application output for display on the GUI has a current processor utilization that indicates user activity associated with the device 200a; and a display object obtain circuit 211a operable to obtain a display object from a set of display object(s) 213a based on the current user activity or status.

In FIG. 2B, the device 200b implements various functional means, units, or modules (e.g., via the processing circuitry 301c in FIG. 3C, via the processing circuitry 501 in FIG. 5B, via software code, or the like), or circuits. In one embodiment, these functional means, units, modules, or circuits (e.g., for implementing the method(s) herein) may include for instance: a receiver circuit 201b operable to receive a display object or an indication associated with the display object that represents a current user activity or status or to receive an indication that requests one or more images that represents the current user activity or status of a wearer of the device 200b; an image capture circuit 203b operable to capture one or more images from an optical sensor(s) 205b disposed in the device 200b; a send circuit 207b operable to send one or more images representing the current user activity or status; a display object obtain circuit 209b operable to obtain a display object from a set of display object(s) 213b based on the display object indication; a display object select circuit 209b operable to select a display object from the set of display object(s) 213b based on the display object indication or to process the one or more images to obtain a display object; and a display circuit 215b operable to send for display on a display 217b the display object representing the current user activity or status.

FIGS. 3A-B illustrate embodiments of a first network node 300a-b in accordance with various aspects as described herein. In FIG. 3A, the device 300a may include processing circuitry 301a that is operably coupled to one or more of the following: memory 303a and network communications circuitry 311a. The communication circuitry 311a is configured to transmit and/or receive information to and/or from one or more other nodes over a network or peer-to-peer communication link via any communication technology. The processing circuitry 301a is configured to perform processing described herein, such as by executing instructions and accessing information stored in the memory 303a. The memory 303a is configured to include display object(s) 305a. The processing circuitry 303a in this regard may implement certain functional means, units, or modules.

Figure 5A:
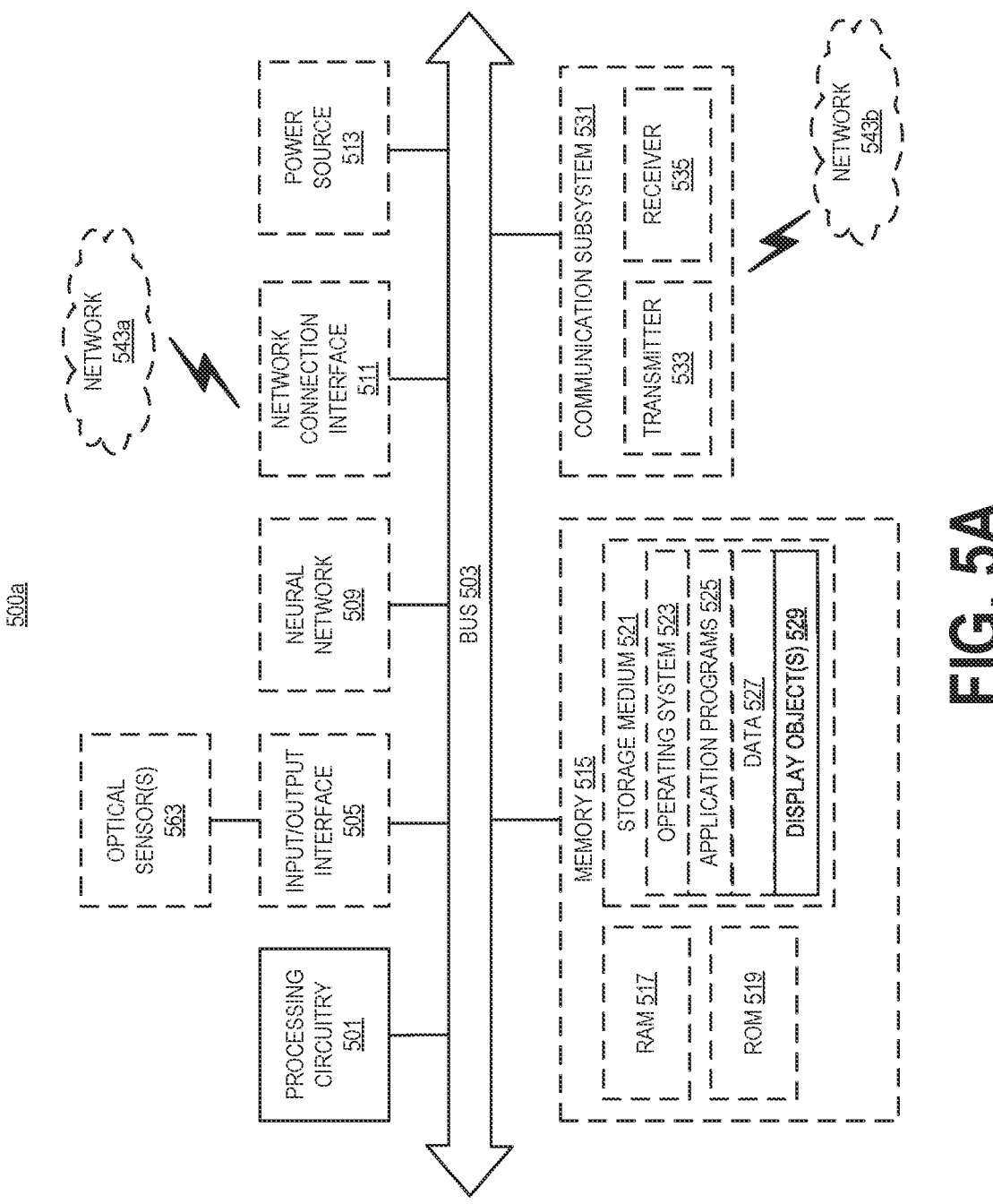
FIGS. 5A-B illustrate other embodiments of a first network node and an ear wearable device, respectively, in accordance with various aspects as described herein.

In FIG. 3B, the device 300b implements various functional means, units, or modules (e.g., via the processing circuitry 301a in FIG. 3A, via the processing circuitry 501 in FIG. 5A, via software code, or the like). In one embodiment, these functional means, units, or modules (e.g., for implementing the method(s) described herein) may include for instance: a receiving module 321b for receiving one or more images representing the current user activity or status; a display object obtaining module 323b for obtaining a display object based on the current user activity or status; a user activity determining module 325b for determining the current user activity or status based on the one or more images or an active application; an active application determining module 327b for determining an application is output for display on a GUI of the device 300b; a processor utilization determining module 329b for determining the application output for display has a current processor utilization that indicates user activity associated with the device 300b; and a sending module 331b for sending an indication that requests one or more images representing the current user activity or status of a wearer of an ear wearable device or sending a display object or a display object indication that represents the current user activity or status.

FIGS. 3C-D illustrate embodiments of an ear wearable device 300c-d in accordance with various aspects as described herein. In FIG. 3C, the device 300*c* may include processing circuitry 301*c* that is operably coupled to one or more of the following: memory 303*c* and network communications circuitry 311*c*. The communication circuitry 311*c* is configured to transmit and/or receive information to and/or from one or more other nodes over a network or peer-to-peer communication link via any communication technology. The processing circuitry 301*c* is configured to perform processing described herein, such as by executing instructions and accessing information stored in the memory 303*c*. The memory 303*c* may be configured to include display object(s) 305*c*. The processing circuitry 303*c* in this regard may implement certain functional means, units, or modules.

Figure 5B:
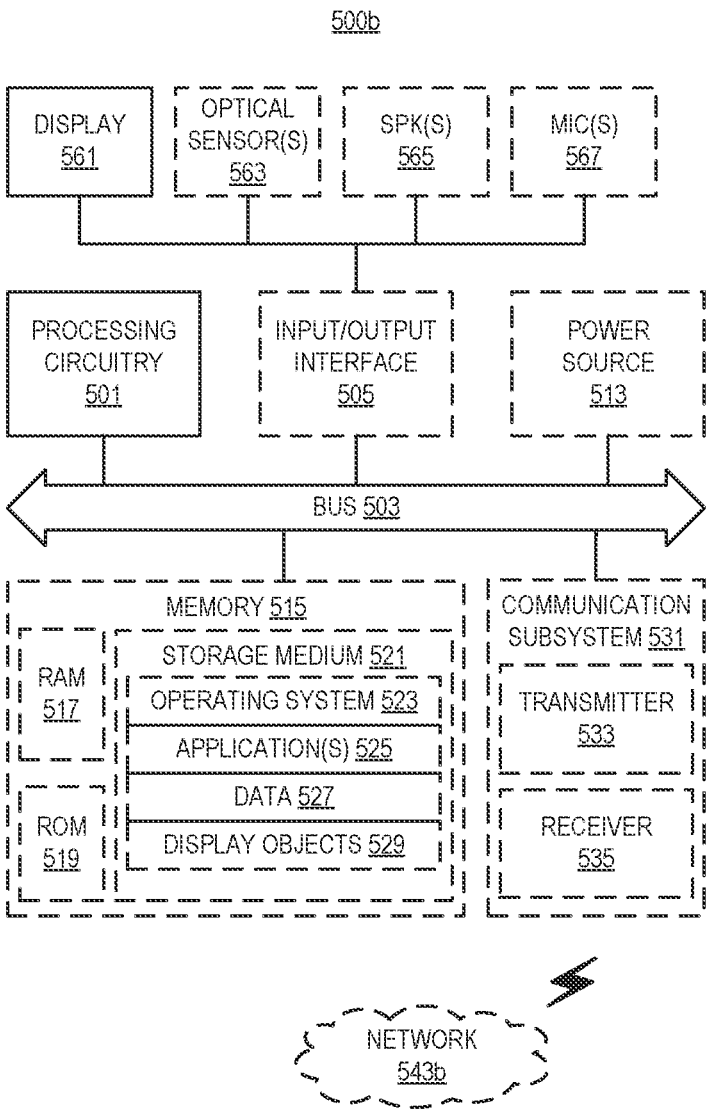

In FIG. 3D, the device 300*d* implements various functional means, units, or modules (e.g., via the processing circuitry 301*c* in FIG. 3C, via the processing circuitry 501 in FIG. 5B, via software code, or the like). In one embodiment, these functional means, units, or modules (e.g., for implementing the method(s) described herein) may include for instance: a receiving module 321*d* for receiving a display object or a display object indication that represents a current user activity or status or receiving an indication that requests one or more images representing the current user activity or status of a wearer of the device 300*d*; an image capturing module 323*d* for capturing one or more images with a viewing angle consistent with a user viewing angle associated with the device 300*d*; a display object obtaining module 325*d* for obtaining a display object; a display object selecting module 327*d* for selecting a display object from a set of display objects; and a sending module 329*d* for sending one or more images representing the current user activity or status.

FIG. 4A illustrates one embodiment of a method 400*a* performed by a first network node 101*b*, 200*a*, 300*a-b*, 500*a* of visually indicating a current user activity or status of a current user via an ear wearable device in accordance with various aspects as described herein. However, it should be understood that portions of the method 400*a* may be distributed among multiple devices. At block 401*a*, the method 400*a* may include sending, to an ear wearable device over a wireless communication channel or a second network node over a network, an indication that requests one or more images representing current user activity or status associated with the ear wearable device, with an optical sensor of the ear wearable device or the second network node having a viewing angle towards the current user activity and being operable to capture the one or more images.

At block 403*a*, the method 400*a* may include receiving from the ear wearable device over the wireless communication channel or the second network node over the network, the one or more images. At block 405*a*, the method 400*a* may include determining the current user activity or status based on the one or more images. At block 407*a*, the method 400*a* may include determining the current user activity or status based on an active application output for display on a graphical user interface of the network node that has a current processor utilization that indicates user activity associated with the network node.

At block 409*a*, the method 400*a* may include obtaining the display object based on the current user activity or status. In addition, the method 400*a* may include selecting the display object from a set of display objects based on the current user activity or status, as represented by block 411*a*. Also, the method 400*a* may include generating the display object based on the active application of the network node, as represented by block 413*a*. Furthermore, the method 400*a* may include converting the display object to conform to one or more characteristics of the display of the ear wearable device 121*b*, as represented by block 415*a*. At block 417*a*, the method 400*a* includes sending to the ear wearable device over the wireless communication channel, a display object or an indication associated with the display object that represents the current user activity or status, with the display object being configured for display on the display of the ear wearable device so as to visually indicate the current user activity or status.

FIG. 4B illustrates one embodiment of a method 400*b* performed by an ear wearable device 121*b*, 200*b*, 300*c-d*, 500*b* of visually indicating a current user activity or status of a current user via an ear wearable device in accordance with various aspects as described herein. However, it should be understood that portions of the method 400*b* may be distributed among multiple devices. At block 401*b*, the method 400*b* may include receiving, from a network node over a wireless communication channel, an indication that requests one or more images representing current user activity or status, with the display being configured to be viewed while the ear wearable device is worn and the optical sensor being configured with a viewing angle towards the current user activity or status and operable to capture the one or more images. At block 403*b*, the method 400*b* may include capturing, by the optical sensor, the one or more images. At block 405*b*, the method 400*b* may include sending to the network node over the wireless communication channel, the one or more images representing the current user activity or status, with the network node being operable to determine the current user activity or status from the one or more images.

At block 407*b*, the method 400*b*, includes receiving from the network node over the wireless communication channel, a display object or an indication associated with the display object that represents the current user activity or status, with the display object being configured for display on the display of the ear wearable device so as to visually indicate the current user activity or status. At block 409*b*, the method 400*b* may include obtaining the display object based on the display object indication. In addition, the method 400*b* may include selecting the display object from a set of display objects stored in memory of the ear wearable device, as represented by block 411*b*. At block 413*b*, the method 400*b* may include processing the one or more images for display on the display to obtain a processed image object. At block 415*b*, the method 400*b* may include sending for display on the display, the processed image object.

FIG. 5A illustrates another embodiment of a network node device 500*a* in accordance with various aspects as described herein. In FIG. 5A, device 500*a* includes processing circuitry 501 that is operatively coupled to input/output interface 505, neural network circuit 509, network connection interface 511, power source 513, memory 515 including random access memory (RAM) 517, read-only memory (ROM) 519, and storage medium 521 or the like, communication subsystem 531, and/or any other component, or any combination thereof. Storage medium 521 may include operating system 523, application program(s) 525, data 527, and display object(s) 529. In other embodiments, storage medium 521 may include other similar types of information. Certain network node devices may utilize all of the components shown in FIG. 5A and FIG. 5B, or only a subset of the components. The level of integration between the components may vary from one device to another device. Further, certain devices may contain multiple instances of a component, such as multiple processors, memories, neural networks, network connection interfaces, transceivers, etc.

In FIG. 5A, processing circuitry 501 may be configured to process computer instructions and data. Processing circuitry 501 may be configured to implement any sequential state machine operative to execute machine instructions stored as machine-readable computer programs in the memory, such as one or more hardware-implemented state machines (e.g., in discrete logic, FPGA, ASIC, etc.); programmable logic together with appropriate firmware; one or more stored program, general-purpose processors, such as a microprocessor or Digital Signal Processor (DSP), together with appropriate software; or any combination of the above. For example, the processing circuitry 501 may include two central processing units (CPUs). Data may be information in a form suitable for use by a computer.

In the depicted embodiment, input/output interface 505 may be configured to provide a communication interface to an input device, output device, or input and output device. The device 500*a* may be configured to use an output device via input/output interface 505. For example, the output device may be a speaker, a sound card, a video card, a display, a monitor, a printer, an actuator, an emitter, a smartcard, a light emitting element (LED) display, another output device, or any combination thereof. The device 500*a* may be configured to use an input device via input/output interface 505 to allow a user to capture information into the device 500*a*. The input device may include a touch-sensitive or presence-sensitive display, an optical or image sensor 563 (e.g., a digital camera, a digital video camera, a web camera, etc.), a microphone, a sensor, a mouse, a trackball, a directional pad, a trackpad, a scroll wheel, a smartcard, and the like. The presence-sensitive display may include a capacitive or resistive touch sensor to sense input from a user. A sensor may be, for instance, an accelerometer, a gyroscope, a tilt sensor, a force sensor, a magnetometer, an optical or image sensor, an infrared sensor, a proximity sensor, another like sensor, or any combination thereof.

In FIG. 5A, the neural network 509 may be configured to learn to perform tasks by considering examples such as performing human activity recognition of users based on training images of different simple or complex activities (e.g., walking, interactions, etc.). The network connection interface 511 may be configured to provide a communication interface to network 543*a*. The network 543*a* may encompass wired and/or wireless networks such as a local-area network (LAN), a wide-area network (WAN), a computer network, a wireless network, a telecommunications network, another like network or any combination thereof. For example, network 543*a* may comprise a Wi-Fi network. The network connection interface 511 may be configured to include a receiver and a transmitter interface used to communicate with one or more other devices over a communication network according to one or more communication protocols, such as Ethernet, TCP/IP, SONET, ATM, or the like. The network connection interface 511 may implement receiver and transmitter functionality appropriate to the communication network links (e.g., optical, electrical, and the like). The transmitter and receiver functions may share circuit components, software or firmware, or alternatively may be implemented separately.

The RAM 517 may be configured to interface via a bus 503 to the processing circuitry 501 to provide storage or caching of data or computer instructions during the execution of software programs such as the operating system, application programs, and device drivers. The ROM 519 may be configured to provide computer instructions or data to processing circuitry 501. For example, the ROM 519 may be configured to store invariant low-level system code or data for basic system functions such as basic input and output (I/O), startup, or reception of keystrokes from a keyboard that are stored in a non-volatile memory. The storage medium 521 may be configured to include memory such as RAM, ROM, programmable read-only memory (PROM), erasable programmable read-only memory (EPROM), electrically erasable programmable read-only memory (EEPROM), magnetic disks, optical disks, floppy disks, hard disks, removable cartridges, or flash drives. In one example, the storage medium 521 may be configured to include an operating system 523, an application program 525 such as bar code decoder, a widget or gadget engine or another application, a data file 527, and a display object(s) 529. The storage medium 521 may store, for use by the device 500*a*, any of a variety of various operating systems or combinations of operating systems.

The storage medium 521 may be configured to include a number of physical drive units, such as redundant array of independent disks (RAID), floppy disk drive, flash memory, USB flash drive, external hard disk drive, thumb drive, pen drive, key drive, high-density digital versatile disc (HD-DVD) optical disc drive, internal hard disk drive, Blu-Ray optical disc drive, holographic digital data storage (HDDS) optical disc drive, external mini-dual in-line memory module (DIMM), synchronous dynamic random access memory (SDRAM), external micro-DIMM SDRAM, smartcard memory such as a subscriber identity module or a removable user identity (SIM/RUIM) module, other memory, or any combination thereof. The storage medium 521 may allow the device 500 to access computer-executable instructions, application programs or the like, stored on transitory or non-transitory memory media, to off-load data, or to upload data. An article of manufacture, such as one utilizing a communication system may be tangibly embodied in the storage medium 521, which may comprise a device readable medium.

In FIG. 5A, the processing circuitry 501 may be configured to communicate with network 543*b* or over a peer-to-peer communication link using the communication subsystem 531. The network 543*a* and the network 543*b* may be the same network or networks or different network or networks. The communication subsystem 531 may be configured to include one or more transceivers used to communicate with the network 543*b*. For example, the communication subsystem 531 may be configured to include one or more transceivers used to communicate with one or more remote transceivers of another device capable of wireless communication according to one or more communication protocols, such as IEEE 802.11, CDMA, WCDMA, GSM, LTE, UTRAN, WiMax, or the like. Each transceiver may include transmitter 533 and/or receiver 535 to implement transmitter or receiver functionality, respectively, appropriate to the RAN links (e.g., frequency allocations and the like). Further, transmitter 533 and receiver 535 of each transceiver may share circuit components, software or firmware, or alternatively may be implemented separately.

In the illustrated embodiment, the communication functions of the communication subsystem 531 may include data communication, voice communication, multimedia communication, short-range communications such as Bluetooth, near-field communication, location-based communication such as the use of the global positioning system (GPS) to determine a location, another like communication function, or any combination thereof. For example, the communication subsystem 531 may include cellular communication, Wi-Fi communication, Bluetooth communication, and GPS communication. The network 543*b* may encompass wired and/or wireless networks such as a local-area network (LAN), a wide-area network (WAN), a computer network, a wireless network, a telecommunications network, another like network or any combination thereof. For example, the network 543*b* may be a cellular network, a Wi-Fi network, and/or a near-field network. The power source 513 may be configured to provide alternating current (AC) or direct current (DC) power to components of the device 500.

FIG. 5B illustrates another embodiment of an ear wearable device 500*b* in accordance with various aspects as described herein. In FIG. 5B, device 500*b* includes processing circuitry 501 that is operatively coupled to input/output interface 505, power source 513, memory 515 including random access memory (RAM) 517, read-only memory (ROM) 519, and storage medium 521, communication subsystem 531, and/or any other component, or any combination thereof. In some implementations, the communication subsystem 531 is configured to provide a wireless communication channel with the device 500*a* via the network 543*b* or over a peer-to-peer communication link. Storage medium 521 may include operating system 523, application program 525, data 527, or the like. Certain ear wearable devices may utilize all of the components shown in FIG. 5A and FIG. 5B, or only a subset of the components. The level of integration between the components may vary from one device to another device. Further, certain devices may contain multiple instances of a component, such as multiple processors, memories, neural networks, network connection interfaces, transceivers, etc.

In the depicted embodiment, input/output interface 505 may be configured to provide a communication interface to an input device, output device, or input and output device. The device 500*a* may be configured to use an output device via input/output interface 505. For example, the output device may be a speaker 565, a sound card, a video card, a display 561, a monitor, a printer, an actuator, an emitter, a smartcard, a light emitting element (LED) display, another output device, or any combination thereof. The device 500*a* may be configured to use an input device via input/output interface 505 to allow a user to capture information into the device 500*a*. The input device may include a touch-sensitive or presence-sensitive display 561, an optical or image sensor 563 (e.g., a digital camera, a digital video camera, a web camera, etc.), a microphone 567, a sensor, a mouse, a trackball, a directional pad, a trackpad, a scroll wheel, a smartcard, and the like.

The features, benefits and/or functions described herein may be implemented in one of the components of the device 500*a-b* or partitioned across multiple components of the device 500*a-b*. Further, the features, benefits, and/or functions described herein may be implemented in any combination of hardware, software or firmware. In one example, communication subsystem 531 may be configured to include any of the components described herein. Further, the processing circuitry 501 may be configured to communicate with any of such components over the bus 503. In another example, any of such components may be represented by program instructions stored in memory that when executed by the processing circuitry 501 perform the corresponding functions described herein. In another example, the functionality of any of such components may be partitioned between the processing circuitry 501 and the communication subsystem 531. In another example, the non-computationally intensive functions of any of such components may be implemented in software or firmware and the computationally intensive functions may be implemented in hardware.

Those skilled in the art will also appreciate that embodiments herein further include corresponding computer programs.

A computer program comprises instructions which, when executed on at least one processor of an apparatus, cause the apparatus to carry out any of the respective processing described above. A computer program in this regard may comprise one or more code modules corresponding to the means or units described above.

Embodiments further include a carrier containing such a computer program. This carrier may comprise one of an electronic signal, optical signal, radio signal, or computer readable storage medium.

In this regard, embodiments herein also include a computer program product stored on a non-transitory computer readable (storage or recording) medium and comprising instructions that, when executed by a processor of an apparatus, cause the apparatus to perform as described above.

Embodiments further include a computer program product comprising program code portions for performing the steps of any of the embodiments herein when the computer program product is executed by a computing device. This computer program product may be stored on a computer readable recording medium.

Additional embodiments will now be described. At least some of these embodiments may be described as applicable in certain contexts for illustrative purposes, but the embodiments are similarly applicable in other contexts not explicitly described.

In one exemplary embodiment, a method comprises, by an ear wearable device that includes a display that is configured to be viewable while the ear wearable device is worn, receiving, from a first network node over a wireless communication channel, a display object or an indication associated with the display object that represents a current user activity or status, with the display object being configured for display on the display of the ear wearable device so as to visually indicate the current user activity or status, the first network node being operable to determine the current user activity or status.

In another exemplary embodiment, the method further includes selecting the display object from a set of display objects stored in non-volatile memory of the ear wearable device based on the display object indication.

In another exemplary embodiment, the method further includes sending, by a processor of the ear wearable device, for display on the display, the display object.

In another exemplary embodiment, the method further includes receiving, by the ear wearable device, from the first network node over the wireless communication channel, an indication that requests one or more images representing the current user activity or status of the user of the ear wearable device, with the first network node being operable to determine the current user activity or status from the one or more images.

In another exemplary embodiment, the method further includes capturing, by an optical sensor disposed in the ear wearable device with a viewing angle consistent with a user viewing angle associated with the ear wearable device, one or more images. Additionally, the method comprises, sending, by the ear wearable device, to the first network node over the wireless communication channel, one or more images representing the current user activity or status, with the first network node being operable to determine the current user activity or status from the one or more images.

In another exemplary embodiment, the method further includes wherein the receiving the display object or the indication of the display object is responsive to sending the one or more images.

In another exemplary embodiment, the method further includes processing the one or more images for display on the display to obtain a processed image object. Additionally, the method comprises, sending, by a processor of the ear wearable device, for display on the display, the one or more images representing the current user activity or status.

In another exemplary embodiment, the method further includes sending, by the ear wearable device, to a second network node over the wireless communication channel, the one or more images responsive to receiving from the second network node an indication that requests the one or more images.

In another exemplary embodiment, the method further includes receiving, by the ear wearable device, from the second network node over the wireless communication channel, another display object or an indication associated with the other display object.

In another exemplary embodiment, the method further includes wherein the display object includes an image, wherein the image is configured to conform to a shape of the display of the ear wearable device.

In another exemplary embodiment, the method further includes wherein the display object includes textual data that indicates the current user activity or status.

In another exemplary embodiment, the method further includes wherein the display object includes a quick response (QR) code that indicates the current user activity or status.

In another exemplary embodiment, the method further includes wherein the display object includes an emoji that indicates the current user activity or status.

In one exemplary embodiment, an ear wearable device, comprising: processing circuitry and a memory, the memory comprising instructions executable by the processing circuitry whereby the processing circuitry is configured to: receive, from the first network node, a display object or an indication of the display object that represents a current user activity or status, with the display object being configured for display on a display of the ear wearable device, with the display being configured to be viewable while the ear wearable device is worn so as to visually indicate the current user activity or status.

In one exemplary embodiment, a method comprises, by a first network node, sending, to an ear wearable device over a wireless communication channel, a display object or an indication associated with the display object that represents current user activity or status determined by the first network node, with the ear wearable device having a display that is configured to display the display object so as to visually indicate the current user activity or status while the ear wearable device is worn.

In another exemplary embodiment, the method further includes receiving, by the first network node, from the ear wearable device over the wireless communication channel or the second network node over the network, one or more images representing the current user activity or status.

In another exemplary embodiment, the method further includes determining the current user activity or status based on the one or more images.

In another exemplary embodiment, the method further includes determining the current user activity or status based on an active application output for display on a graphical user interface of the first network node that has a current processor utilization that indicates user activity associated with the first network node.

In another exemplary embodiment, the method further includes obtaining the display object based on the current user activity or status.

In one exemplary embodiment, a first network node comprising: processing circuitry and a memory, the memory containing instructions executable by the processing circuitry whereby the processor is configured to: send, to an ear wearable device over a wireless communication channel, a display object or an indication associated with the display object that represents current user activity or status determined by the first network node, with the ear wearable device having a display that is configured to display the display object so as to visually indicate the current user activity or status while the ear wearable device is worn.

The previous detailed description is merely illustrative in nature and is not intended to limit the present disclosure, or the application and uses of the present disclosure. Furthermore, there is no intention to be bound by any expressed or implied theory presented in the preceding field of use, background, summary, or detailed description. The present disclosure provides various examples, embodiments and the like, which may be described herein in terms of functional or logical block elements. The various aspects described herein are presented as methods, devices (or apparatus), systems, or articles of manufacture that may include a number of components, elements, members, modules, nodes, peripherals, or the like. Further, these methods, devices, systems, or articles of manufacture may include or not include additional components, elements, members, modules, nodes, peripherals, or the like.

Furthermore, the various aspects described herein may be implemented using standard programming or engineering techniques to produce software, firmware, hardware (e.g., circuits), or any combination thereof to control a computing device to implement the disclosed subject matter. It will be appreciated that some embodiments may be comprised of one or more generic or specialized processors such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the methods, devices and systems described herein. Alternatively, some or all functions could be implemented by a state machine that has no stored program instructions, or in one or more application specific integrated circuits (ASICs), in which each function or some combinations of certain of the functions are implemented as custom logic circuits. Of course, a combination of the two approaches may be used. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The term "article of manufacture" as used herein is intended to encompass a computer program accessible from any computing device, carrier, or media. For example, a computer-readable medium may include: a magnetic storage device such as a hard disk, a floppy disk or a magnetic strip; an optical disk such as a compact disk (CD) or digital versatile disk (DVD); a smart card; and a flash memory device such as a card, stick or key drive. Additionally, it should be appreciated that a carrier wave may be employed to carry computer-readable electronic data including those used in transmitting and receiving electronic data such as electronic mail (e-mail) or in accessing a computer network such as the Internet or a local area network (LAN). Of course, a person of ordinary skill in the art will recognize many modifications may be made to this configuration without departing from the scope or spirit of the subject matter of this disclosure.

Throughout the specification and the embodiments, the following terms take at least the meanings explicitly associated herein, unless the context clearly dictates otherwise. Relational terms such as "first" and "second," and the like may be used solely to distinguish one entity or action from another entity or action without necessarily requiring or implying any actual such relationship or order between such entities or actions. The term "or" is intended to mean an inclusive "or" unless specified otherwise or clear from the context to be directed to an exclusive form. Further, the terms "a," "an," and "the" are intended to mean one or more unless specified otherwise or clear from the context to be directed to a singular form. The term "include" and its various forms are intended to mean including but not limited to. References to "one embodiment," "an embodiment," "example embodiment," "various embodiments," and other like terms indicate that the embodiments of the disclosed technology so described may include a particular function, feature, structure, or characteristic, but not every embodiment necessarily includes the particular function, feature, structure, or characteristic. Further, repeated use of the phrase "in one embodiment" does not necessarily refer to the same embodiment, although it may. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. A device or structure that is "configured" in a certain way is configured in at least that way, but may also be configured in ways that are not listed.

What is claimed is:

1. A method, comprising:
by an ear wearable device that includes a processing circuitry operably coupled to a memory, a communication interface operable to communicate over a wireless communication channel, a display device operable to display and configured to be viewable while the ear wearable device is worn and an optical sensor disposed on the ear wearable device and having a viewing angle directed outward from the ear wearable device and operable to capture image data,
capturing, by the optical sensor, image data representing an external environment or activity proximate the ear wearable device;
sending, by the processing circuitry, via the communication interface over the wireless communication channel, to a first network node device, the image data, with the first network node device being operable to determine a current activity or status associated with the ear wearable device based on the image data;
receiving, by the processing circuitry, via the communication interface over the wireless communication channel, from the first network node device, an activity indication that identifies the current activity or status based on the image data;

obtaining, by the processing circuitry, from a set of display objects that are stored in the memory and configured to visually represent activities or statuses on the display device, a first display object that corresponds to the current activity or status; and
outputting, by the processing circuitry, for display on the display device, the first display object so as to visually indicate the current activity or status.

2. The method of claim 1, wherein the first display object represents a status associated with the ear wearable device.

3. The method of claim 1, further comprising:
receiving, by the processing circuitry, via the communication interface over the wireless communication channel, from the first network node device, an indication that requests one or more images representing the current activity or status associated with the ear wearable device, with the first network node device being enabled to determine the current activity or status from the one or more images.

4. The method of claim 1, further comprising:
capturing, by the optical sensor disposed in the ear wearable device having the viewing angle towards the current activity or status, one or more images; and
sending, by the processing circuitry, via the communication interface over the wireless communication channel, to the first network node device, the one or more images.

5. The method of claim 4, wherein the step of obtaining the first display object or a first display object indication is responsive to sending the one or more images.

6. The method of claim 4, wherein the capturing and the sending of the one or more images is performed at a certain time interval so that the first network node device is enabled to determine and update the current activity or status on the display device at the certain time interval.

7. The method of claim 4, further comprising:
processing the one or more images for display on the display device to obtain a processed image object; and
outputting, by the processing circuitry, for display on the display device, the processed image object.

8. The method of claim 4, further comprising:
receiving, by the processing circuitry, via the communication interface over the wireless communication channel, from a second network node device, an indication that requests one or more second images;
capturing, by the optical sensor disposed in the ear wearable device, the one or more second images; and
sending, by the processing circuitry, via the communication interface over the wireless communication channel, to the second network node device, the one or more second images.

9. The method of claim 8, further comprising:
receiving, by the processing circuitry, via the communication interface over the wireless communication channel, from the second network node device, a second display object of the set of display objects or a second display object indication.

10. The method of claim 1, wherein the first display object includes an image, wherein the image is configured to conform to a shape and a resolution of the display device.

11. The method of claim 1, wherein the first display object includes a quick response (QR) code that indicates the current activity or status.

12. The method of claim 1, wherein the first display object includes an emoji that indicates the current activity or status.

13. An ear wearable device, comprising:
a memory;

US 12,616,393 B2

17 a communication interface operable to communicate over a wireless communication channel;

a display device operable to display and configured to be viewable while the ear wearable device is worn;

an optical sensor disposed on the ear wearable device, having a viewing angle directed outward from the ear wearable device and operable to capture image data;

a processing circuitry operably coupled to the memory, the communication interface, the display device and the optical sensor; and wherein the memory includes instructions executable by the processing circuitry whereby the processing circuitry is configured to:

obtain, from the optical sensor, image data representing an external environment or activity proximate the ear wearable device;

send, via the communication interface over the wireless communication channel, to a first network node device, the image data, with the first network node device being operable to determine a current activity or status associated with the ear wearable device based on the image data;

receive, via the communication interface over the wireless communication channel, from the first network node device, an activity indication that identifies the current activity or status based on the image data;

obtain, from a set of display objects that are stored in the memory and configured to visually represent activities or statuses on the display device, a first display object that corresponds to the current activity or status; and output, for display on the display device, the first display object so as to visually indicate the current activity or status associated with the ear wearable device.

14. A method, comprising:

by a first network node device that includes processing circuitry operably coupled to a memory and a communication interface operable to communicate over a wireless communication channel with an ear wearable device, receiving, by the processing circuitry, via the communication interface over the wireless communication channel, from the ear wearable device, image data captured by an optical sensor disposed on the ear wearable device and having a viewing angle directed outward from the ear wearable device, the image data representing an external environment or activity proximate the ear wearable device;

determining, by the processing circuitry, a current activity or status associated with the ear wearable device based on the received image data;

sending, by the processing circuitry, via the communication interface over the wireless communication channel, to the ear wearable device, an activity indication that identifies the current activity or status to enable the ear wearable device to select a first display object of a set of display objects configured to visually represent activities or statuses on a display device of the ear wearable device so as to visually indicate the current activity or status while the ear wearable device is worn.

15. The method of claim 14, further comprising:

sending, by the processing circuitry, via the communication interface over the wireless communication channel, to the ear wearable device or a second network node device over a network, an indication that requests one or more images representing the current activity, with an optical sensor of the ear wearable device or the second network node device being configured to have a viewing angle towards the current activity or status and being operable to capture the one or more images.

16. The method of claim 14, further comprising:

receiving, by the processing circuitry, via the communication interface over the wireless communication channel, from the ear wearable device or a second network node device over the network, one or more images representing the current activity or status.

17. The method of claim 16, further comprising:

determining the current activity or status associated with the ear wearable device based on the one or more images.

18. The method of claim 14, further comprising:

determining the current activity or status based on an active application output for display on a graphical user interface of the first network node device that has a current processor utilization that indicates current activity or status associated with the first network node device.

19. The method of claim 14, further comprising:

obtaining the first display object based on the current activity or status associated with the ear wearable device.

20. A first network node device, comprising:

a memory;

a communication interface operable to communicate over a wireless communication channel with an ear wearable device;

a processing circuitry operably coupled to the memory and the communication interface; and wherein the memory includes instructions executable by the processing circuitry whereby the processing circuitry is configured to:

receive, via the communication interface over the wireless communication channel, from the ear wearable device, image data captured by an optical sensor disposed on the ear wearable device and having a viewing angle directed outward from the ear wearable device, the image data representing an external environment or activity proximate the ear wearable device;

determine a current activity or status associated with the ear wearable device based on the received image data;

send, by the processing circuitry, via the communication interface over the wireless communication channel, to the ear wearable device, an activity indication that identifies the current activity or status associated with the ear wearable device; and wherein the activity indication enables the ear wearable device to select a first display object of a set of display objects configured to visually represent activities or statuses on a display device of the ear wearable device so as to visually indicate the current activity or status while the ear wearable device is worn.

* * * * *